United States Patent
Hildebrandt et al.

(10) Patent No.: US 10,779,859 B2
(45) Date of Patent: Sep. 22, 2020

(54) ARRANGEMENT FOR THE ULTRASOUND-ASSISTED MANIPULATION ON THE FEMALE REPRODUCTIVE ORGANS OF LARGE MAMMALS AND USE OF THE ARRANGEMENT

(71) Applicants: Thomas Hildebrandt, Berlin (DE); Arno Schnorrenberg, Woltersdorf (DE)

(72) Inventors: Thomas Hildebrandt, Berlin (DE); Arno Schnorrenberg, Woltersdorf (DE); Ivo Weissmann, Boeblingen (DE)

(73) Assignees: Thomas Hildebrandt, Berlin (DE); Arno Schnorrenberg, Woltersdorf (DE)

( * ) Notice: Subject to any disclaimer, the term of this patent is extended or adjusted under 35 U.S.C. 154(b) by 302 days.

(21) Appl. No.: 15/909,817

(22) Filed: Mar. 1, 2018

(65) Prior Publication Data
US 2018/0250032 A1    Sep. 6, 2018

(30) Foreign Application Priority Data

Mar. 1, 2017    (DE) .......................... 10 2017 002 614

(51) Int. Cl.
*A61B 17/435* (2006.01)
*A61B 10/02* (2006.01)
(Continued)

(52) U.S. Cl.
CPC .............. *A61B 17/435* (2013.01); *A61B 8/12* (2013.01); *A61B 8/4444* (2013.01);
(Continued)

(58) Field of Classification Search
CPC ........... A61B 8/445; A61B 8/12; A61B 10/00; A61B 2010/045; A61B 8/4444;
(Continued)

(56) References Cited

U.S. PATENT DOCUMENTS 5,538,504 A * 7/1996 Linden .................. A61M 25/10
                                                   604/264
2003/0144594 A1* 7/2003 Gellman ................ A61B 1/015
                                                   600/466

FOREIGN PATENT DOCUMENTS

DE      102 03 094 A1    8/2003
EP      1 967 147 A2     9/2008
(Continued)

OTHER PUBLICATIONS

Extended European Search Report dated Jun. 25, 2018 as received in Application No. 18159192.6.

*Primary Examiner* — Christine H Matthews
*Assistant Examiner* — Joshua Daryl D Lannu
(74) *Attorney, Agent, or Firm* — Maschoff Brennan

(57) ABSTRACT

The invention relates to an assembly for ultrasound-assisted manipulation at the female reproductive organs of large mammals, such as rhinoceros, elephant and hippopotamus, and to the use of the assembly. The assembly comprises a support pipe with an end element and a handle piece, a guide pipe provided in the support pipe, a puncture needle, an ultrasound head support provided at the distal end of the support pipe and having accomodators for an ultrasound head and the distal end of the guide pipe, wherein the axis of the ultrasound head and of the distal end of the guide pipe is in each case angled with respect to the horizontal axis of the support pipe such that the position of the tip of the puncture needle is in the ultrasound scan range of the ultrasound head.

20 Claims, 9 Drawing Sheets

(51) Int. Cl.
*A61B 8/00* (2006.01)
*A61B 17/43* (2006.01)
*A61D 19/04* (2006.01)
*A61B 8/12* (2006.01)
*A61B 10/00* (2006.01)
*A61B 8/08* (2006.01)
*A61B 10/04* (2006.01)

(52) U.S. Cl.
CPC .......... *A61B 10/0283* (2013.01); *A61B 17/43* (2013.01); *A61D 19/04* (2013.01); *A61B 8/0841* (2013.01); *A61B 8/445* (2013.01); *A61B 10/00* (2013.01); *A61B 2010/045* (2013.01)

(58) Field of Classification Search
CPC ... A61B 10/0283; A61B 17/43; A61B 17/435; A61B 8/0841; A61D 19/04
See application file for complete search history.

(56) References Cited

FOREIGN PATENT DOCUMENTS

| | | | | |
|---|---|---|---|---|
| EP | 1967147 A2 * | 9/2008 | ......... | A61B 10/0233 |
| JP | H11290358 A | 10/1999 | | |
| WO | 2011/145818 A2 | 11/2011 | | |

* cited by examiner

ARRANGEMENT FOR THE ULTRASOUND-ASSISTED MANIPULATION ON THE FEMALE REPRODUCTIVE ORGANS OF LARGE MAMMALS AND USE OF THE ARRANGEMENT

REFERENCE TO RELATED APPLICATION

This application claims priority to German Patent Application No. 10 2017 002 614.9 filed on Mar. 1, 2017, the entirety of which is incorporated by reference herein.

BACKGROUND

The invention relates to an assembly for ultrasound-assisted manipulation at the female reproductive organs of large mammals, such as rhinoceros, elephant and hippopotamus, and to the use of said assembly. The invention is directed in particular to assisting the reproduction of animal species threated with extinction.

For oocyte recovery from living animals, the so-called ovum pick-up method is known. Said method is based on ultrasonography and is sometimes also referred to as "transvaginal ultrasound-guided follicle puncture". In said method, the sonic head is pushed into the vagina and the ovary is pressed against the probe by the rectally inserted hand. In most cases, a second person punctures the follicle using a cannula arranged in the probe support and collects the ovum.

A device intended for the recovery of oocytes in cows or horses and a method in relation thereto are disclosed by WO 2011145818 A2.

The device comprises a handle having a horizontally arranged guide tube in which a metal cannula is mounted, which metal cannula has, in the axial direction at its front end, an ultrasound head, which is in turn connected to an image reproduction device provided at the upper end of the handle.

At its front end, the metal cannula is surrounded by a cutting blade which is mounted with forward and backward movement and which is intended for cutting through the vaginal wall. An oocyte collection tube takes up the oocytes recovered by means of a needle, which are then transported via a catheter to an oocyte collection container by application of a vacuum. However, the handling of this device becomes complicated. After the operator has placed a hand through the rectum of the animal in order to hold the uterus of the animal, said operator must guide the metal cannula through the vaginal segment of the animal by means of the handle and guide tube in order to ultimately be able to start the collection of the oocytes.

However, this technical solution is not suitable for the collection of oocytes in large animals. A transvaginal follicle method is ruled out in large animals solely because of the "enormous" anatomical proportions compared to horses and cows. For example, in the case of a rhinoceros, the ovaries are approximately 1.5 m within the body.

DE 102 03 094 B4 discloses an inserter for passage through the cervix in large mammals. Although said inserter is suitable for the insemination of such animals, it is not suitable for oocyte recovery and not suitable for embryo transfer either. During the cyclic luteal phase starting directly after ovulation, a mucus which forms covers the zigzag cervical canal and thus prevents the successful introduction of a catheter. A forceful opening of this passage would injure the animal and a local drug-based treatment would lead to fatal damage of the embryo system. In this respect, this option of passage through the cervix for embryo transfer is ruled out from the start.

It is therefore an object of the invention to provide an assembly for ultrasound-assisted manipulation at female reproductive organs of large mammals, which assembly allows said manipulation without use of the vaginal segment of the animal and can be used for the controlled collection of oocytes as well as embryo transfer and intrauterine insemination with avoidance of difficult passage through the uterus channel.

SUMMARY

According to an aspect of the invention there is provided an assembly for ultrasound-assisted manipulation at female reproductive organs of living animals, especially in large mammals. The assembly comprises a support pipe with an end element and a handle piece, a guide pipe provided in the support pipe, a puncture needle, an ultrasound head support provided at the distal end of the support pipe and having accomodators for an ultrasound head and the distal end of the guide pipe, wherein the axis of the ultrasound head and of the distal end of the guide pipe is in each case angled with respect to the horizontal axis of the support pipe such that the position of the tip of the puncture needle is in the ultrasound scan range of the ultrasound head. The ultrasound head may be connected to an image reproduction device.

According to a first configuration, the guide pipe is positioned in the support pipe by means of a fitted positioning element. The puncture needle has a twin-lumen construction for a flushing process and aspiration process, is arranged in the guide pipe in a movable manner, is connected via its proximal end to a momentum initiator in a detachable manner and is fixed in said momentum initiator. The momentum initiator is mounted in a movable manner in the end element in the horizontal direction. There are connecting pieces at the proximal end of the twin-lumen puncture needle for the outer and inner needles, which connecting pieces are connectable to a medical flushing device and to a vacuum pump and a receptacle by means of pieces of tubing. The first configuration is suitable, e.g., for oocyte recovery in large mammals, such as rhinoceros, elephant and hippopotamus.

According to a second configuration, the guide pipe is approximately the length of the support pipe and is mounted at its proximal end in the end element. There is provided within the guide pipe an insertion aid, in which a single-lumen puncture needle is arranged in a horizontally movable manner; and there is provided in the single-lumen puncture needle a movable catheter, which is provided at its proximal end with a Luer-Lock connector. The second configuration is suitable, e.g., for embryo transfer and intrauterine insemination of large mammals, such as rhinoceros, elephant and hippopotamus.

Aspects of the invention are directed in particular to assisting the reproduction of animal species threated with extinction. The invention has put into place for the first time the conditions that make it possible, in large mammals by the rectal route, to collect oocytes, to transfer embryos and to carry out intrauterine insemination of said animals with avoidance of difficult passage through the uterus channel. Aspects of the invention allow a safe and successful recovery of ova in these animal groups, for which the vaginal recovery of ova is ruled out because of the anatomical proportions. By means of the assembly provided by the invention, otherwise infertile female individuals of highly threatened animal species can be additionally included in reproduction via the workaround of in vitro fertilization (IVF), also called test tube fertilization.

In an embodiment, in the assembly, the axis of the ultrasound head is provided at an angle of from 30° to 90° in relation to the horizontal axis of the support pipe.

In an embodiment, a positioning element for the guide pipe has a funnel-shaped receiver for assisting the insertion of a puncture needle into the guide pipe.

A further embodiment of the invention envisages that the ultrasound head support is connected to the support pipe in a detachable manner.

In an embodiment, the twin-lumen puncture needle is surrounded by a piece of Teflon tubing in order to increase slidability in the guide pipe and/or the guide pipe has at its distal end a screw-on end cap.

According to an embodiment of the invention, a momentum initiator is slit at its distal end and the piece of tubing for the flush liquid and the piece of tubing for aspirated oocytes are initially guided in this slit and both pieces of tubing are then guided through a hole provided in the end element of the support pipe.

In an embodiment, the detachable connection between the proximal end of the puncture needle and the momentum initiator is established by means of a sleeve retainer which can be screwed onto the momentum initiator.

A further embodiment of the invention envisages that the route of the distance-guided puncture needle is limited by providing on the momentum initiator a stop element within the support pipe and a stop element outside the support pipe.

In an embodiment, there is provided on the momentum initiator a locking element with locking screw for fixing the passive function of the device and for releasing the active function.

In an embodiment, guide pipes and insertion aids have a two-part construction, are made from stainless steel, and can be connected to one another in a detachable manner.

In an embodiment, the guide pipes can be coated with a plastic suitable therefor in order to increase their slidability.

In an embodiment, the puncture needle, of single-lumen construction, and the catheter are mounted such that they are guidable by hand, and a disposable syringe or a micropipette is provided within the catheter.

According to a further aspect of the invention there is provided a device for collecting oocytes in living animals, especially in large mammals, the device comprising:
a support pipe with a handle piece,
a guide pipe mounted in the support pipe by means of a fitted positioning element, wherein
a twin-lumen puncture needle for a flushing process and aspiration process is arranged in the guide pipe in a movable manner, wherein the puncture needle is connected via its proximal end to a momentum initiator in a detachable manner,
the momentum initiator is mounted in a movable manner in an end element of the support pipe in the horizontal direction and has at its other end a grip element,
the connecting pieces present at the proximal end of the twin-lumen puncture needle for the outer and inner needles are connectable to a medical flushing device and to a vacuum pump and a container for the accommodation of aspirated oocytes by means of pieces of tubing,
an ultrasound head support is provided at the distal end of the support pipe for the accommodation of an ultrasound head and the distal end of the twin-lumen puncture needle,
the axis of the ultrasound head and the distal end of the guide pipe are each angled with respect to the horizontal axis of the support pipe, wherein the guide pipe is angled depending on the axis of the ultrasound head such that the position of the tip of the twin-lumen puncture needle is in the ultrasound scan range during the collection of the oocytes. The ultrasound head may be connected to an image reproduction device.

The inventors deserve credit for the fact that the technical solution found by them has put into place, for the first time, the conditions that make it possible, in large mammals by the rectal route, to collect oocytes and transfer embryos and to carry out intrauterine insemination with avoidance of difficult passage through the uterus channel. Thus, the inventors are making a very important contribution to species conservation and to assisting the reproduction of, in particular, large animals threated with extinction.

By means of the assembly according to the invention, otherwise infertile female individuals of highly threatened animal species can be additionally included in reproduction via the workaround of in vitro fertilization (IVF), also called test tube fertilization. In 1978, the first so-called test tube baby, Louise Brown, was born in England. Her birth introduced a new era in reproductive medicine in humans. The farm animal industry followed relatively quickly.

In species conservation to save highly threatened animal species, this technique is not being used to date, since especially the anatomical proportions in large animal species, such as rhinoceros, elephant and hippopotamus, do not allow the direct transfer of the vaginal aspiration of ova without exposing the patient to an uncalculatable risk. The invention described here allows a safe and successful recovery of ova in these animal groups, for which the vaginal recovery of ova is ruled out because of the anatomical proportions. In humans, several million ovum collections are carried out each year and over 7 million people have been born with use of this method.

The inventors are convinced that their new technical solution will make a contribution to saving species, such as the northern white rhinoceros or the Sumatran rhinoceros, from extinction. Otherwise, the infertile females of the threatened animal species would be lost for ever for breeding.

BRIEF DESCRIPTION OF THE DRAWINGS

The invention will be explained in more detail on the basis of exemplary embodiments with reference to the accompanying drawings in which.

DETAILED DESCRIPTION

Figure 1:
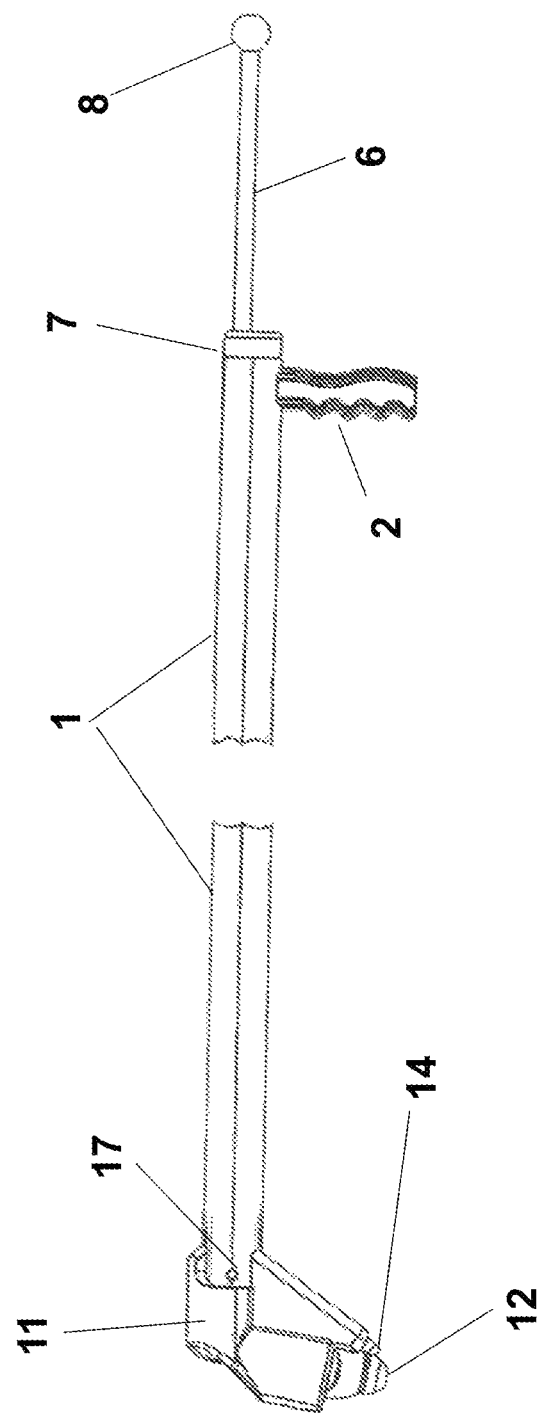
FIG. 1 shows the lateral view of a device according to the invention for oocyte recovery.
Figure 2:
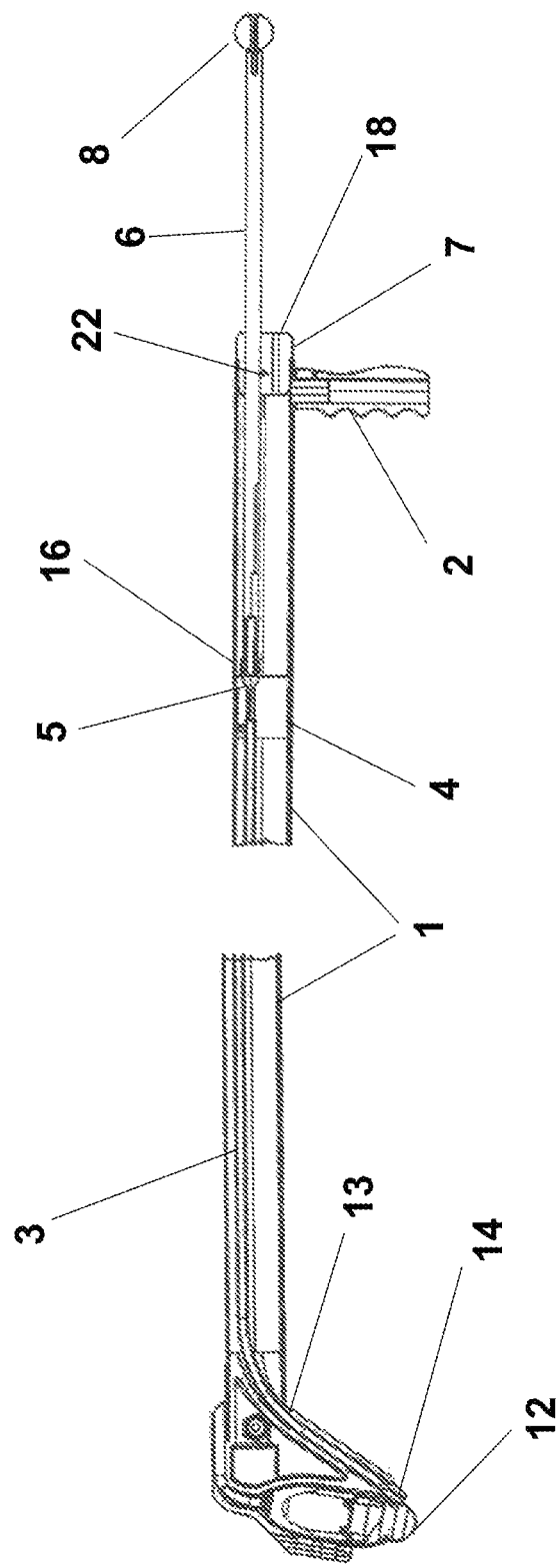
FIG. 2 shows the device according to FIG. 1 with its major components.
Figure 3:
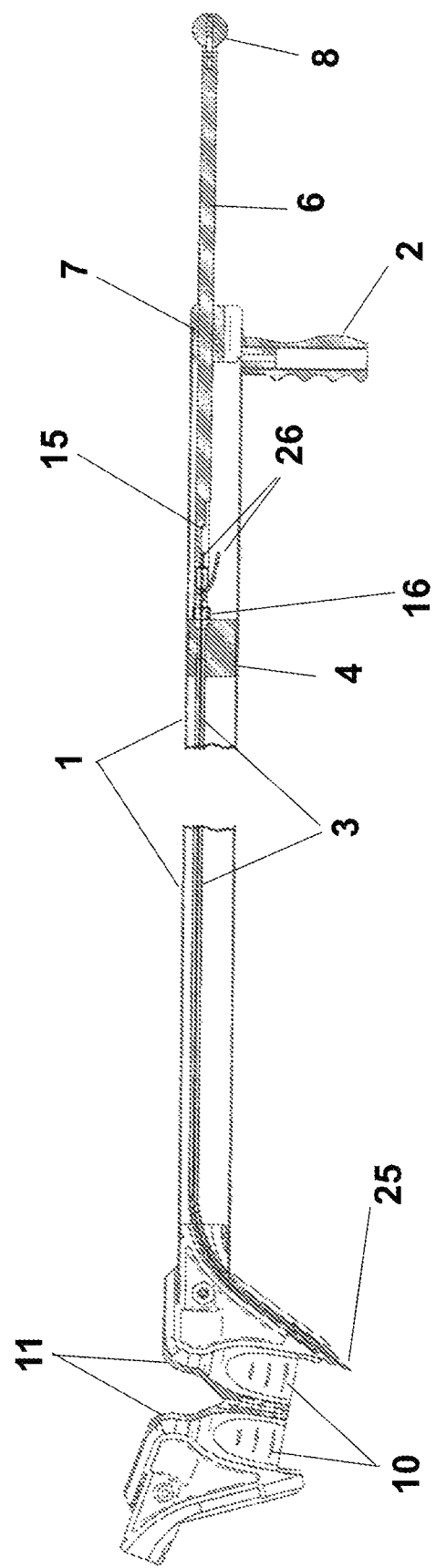
FIG. 3 shows the lateral sectional view of a device according to the invention for oocyte recovery.

As can be identified from FIG. 1 to FIG. 3 and FIG. 5, the assembly according to the invention comprises a support pipe 1 with a handle 2. At its proximal end, said support pipe is provided with an end element 7, through which a momentum initiator 6 with a handle element 8 is guided. At the distal end of the support pipe 1, an ultrasound head support 11 is connected to the support pipe 1 in a detachable manner by means of a screw 17. A hole 22 is provided for the attachment of the handle 2 to the support pipe 1. In the present exemplary embodiment, the assembly according to the invention has a total length of 1400 mm for use for oocyte recovery in a female rhinoceros. Depending on the animal species, the total lengths of the assembly can be in the range between 1300 mm and 2000 mm. In the present example, the outer diameter of the support pipe 1 is about 45 mm.

The support pipe 1 serves to accommodate the guide pipe 3, in which the twin-lumen puncture needle 25 having a length of about 900 mm slides. As can be seen from FIG. 2, the distal end 13 of the guide pipe 3 with the screw-on end cap 14 is angled. What is of particular importance is that the angular deflection of the guide pipe 3 in relation to the axis of the support pipe 1 is provided in such a way that, for oocyte collection, the tip of the twin-lumen puncture needle 25 is in the scan field of the ultrasound head 12. Since the axis of the ultrasound head 12 can have an angle of from 30° to 90° in relation to the horizontal axis of the support pipe 1, a precise manufacture of the ultrasound head support 11 having the accommodators 10 for the ultrasound head 12 and having the accommodators for the guide pipe 3 and the end cap 14 of the guide pipe 3 is imperative.

At its other end, the guide pipe 3 is mounted in the positioning element 4, which is arranged in the support pipe 1 so as to fit. In order to assist the insertion of the twin-lumen puncture needle 25 into the guide pipe 3, the positioning element 4 comprises, as can also be gathered from FIG. 5, the funnel-shaped receiver 5. For a better slidability of the puncture needle 25 in the guide pipe 3, especially in its angled distal end 13, the puncture needle is surrounded by a piece of Teflon tubing. However, it is also possible to use instead a piece of tubing composed of a different plastic which assists slidability.

When the tip of the puncture needle 25 has reached the opening of the end cap 14, the other end of the puncture needle 25 is connected to the momentum initiator 6 in a detachable manner by means of the screw-on sleeve retainer 16. The puncture needle 25 is thus fixed in the momentum initiator 6 at the same time. It is not depicted here that the connecting pieces 26 of the inner hollow needle and of the outer hollow needle of the twin-lumen puncture needle 25 are each connected to a sterile piece of tubing. The pieces of tubing are first guided in the slitted end 15 of the momentum initiator 6 and then guided away from the assembly through the hole 18 in the end element 7.

Figure 9A:
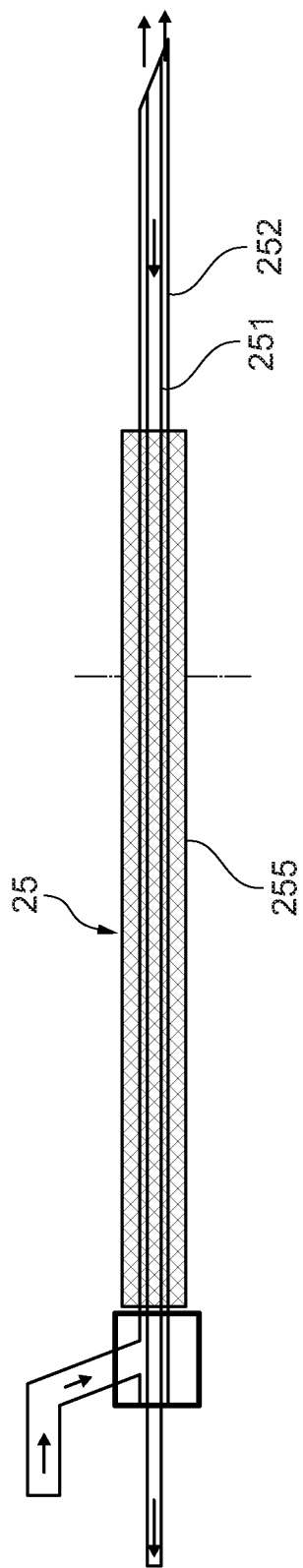
FIG. 9 shows a twin-lumen puncture needle in a schematic manner.
Figure 9B:
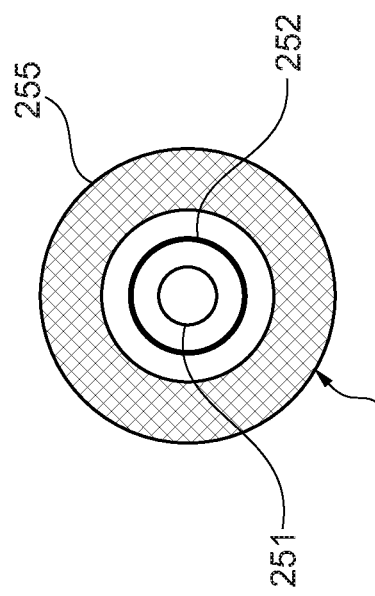

FIG. 9A and FIG. 9B show in a schematic manner in a longitudinal sectional view and a cross-sectional view a puncture needle 25 having a twin-lumen comprising an inner hollow needle 251 and an outer hollow needle 252. The twin-lumen puncture needle 25 may be surrounded by a piece of tubing 255 composed of a plastic which assists slidability. The tubing may be a Teflon® tubing.

Depending on which of the hollow needles is used for the flushing process or for the aspiration of the oocytes, it is connected to a medical flushing device, not depicted here, or to a vacuum pump having a sterile collection container for the accommodation of the aspirated oocytes, not depicted here. What are used are twin-lumen puncture needles having a diameter of from about 1.6 mm to 2.5 mm for the outer hollow needle and from about 1.4 mm to 1.8 mm for the inner hollow needle.

The guidable route of the momentum initiator 6 is limited by two stop elements, not depicted here, which are provided on the momentum initiator 6. Between these two stop elements of the momentum initiator 6 is situated the end element 7, this ensuring that the momentum initiator 6 cannot be unintentionally removed from the support pipe 1. The guidable route of the momentum initiator 6 can be between 60 mm and 120 mm. By means of a locking element, not depicted here, which is provided outside the support pipe 1 on the momentum initiator 6 and which has a bayonet lock or locking screws, it is possible to fix the passive function of the assembly or to re-release the active function of the momentum initiator 6.

Figure 4:
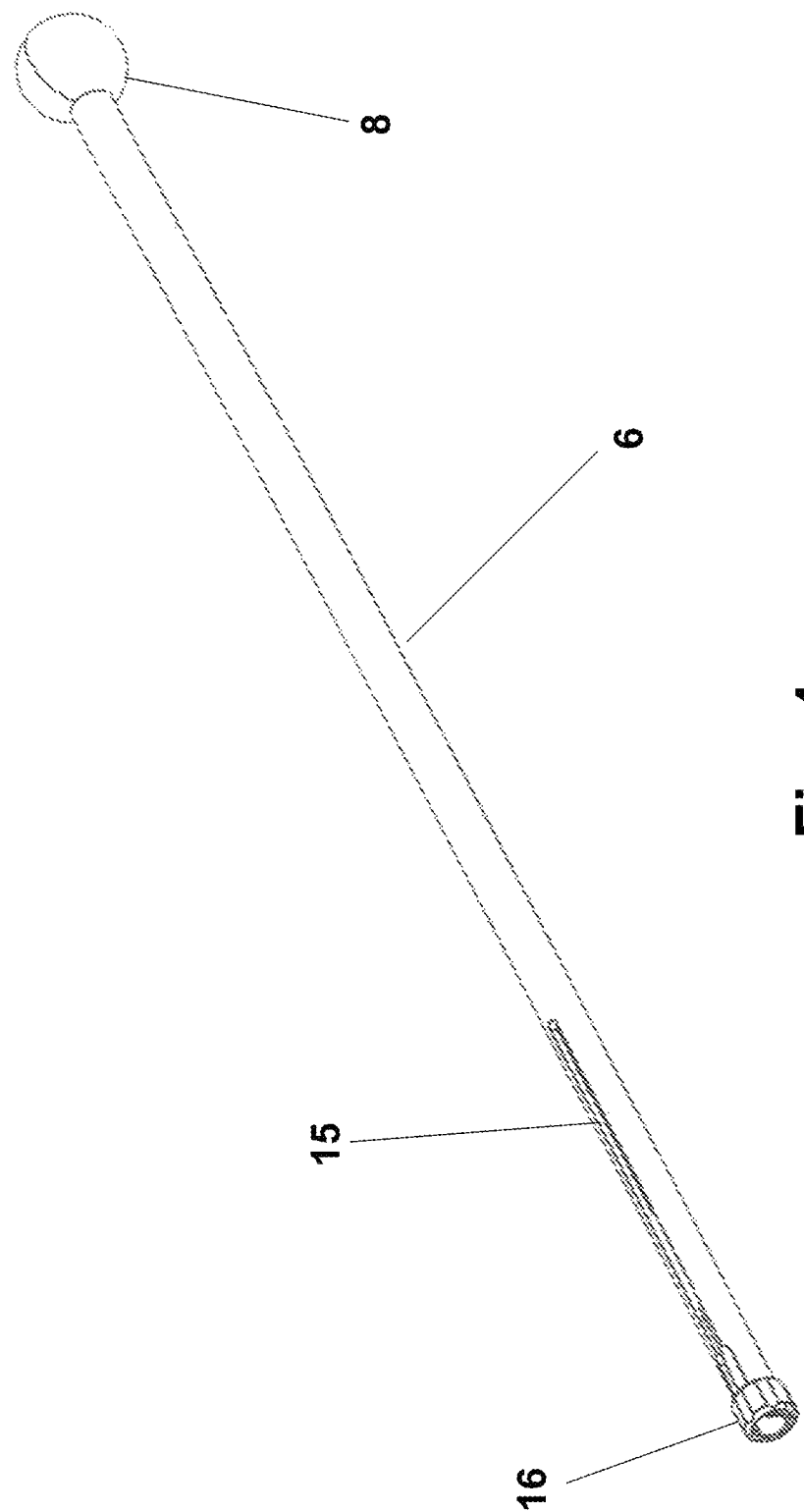
FIG. 4 shows the momentum initiator in perspective view.
Figure 5:
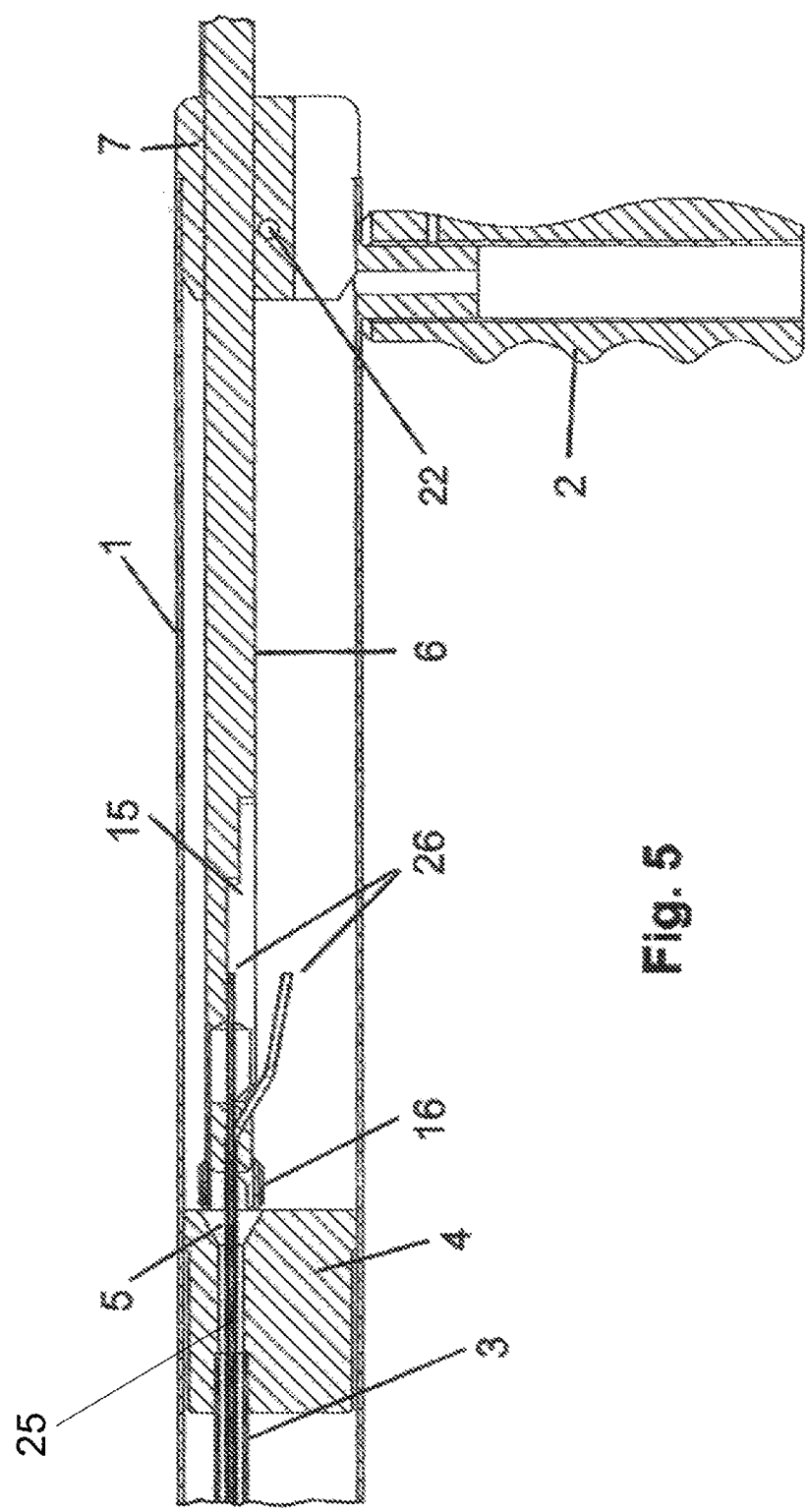
FIG. 5 shows the lateral sectional view of the proximal segment of a device according to the invention for oocyte recovery.

FIG. 4 shows, in perspective view, the momentum initiator 6, which is made from stainless steel. What can be clearly identified is the screw-on sleeve retainer 16 that makes it possible to connect the momentum initiator 6 to the twin-lumen puncture needle 25. The slit 15 serves—as already described—to guide through the sterile pieces of tubing which are to be connected to the connecting pieces 26.

Figure 6:
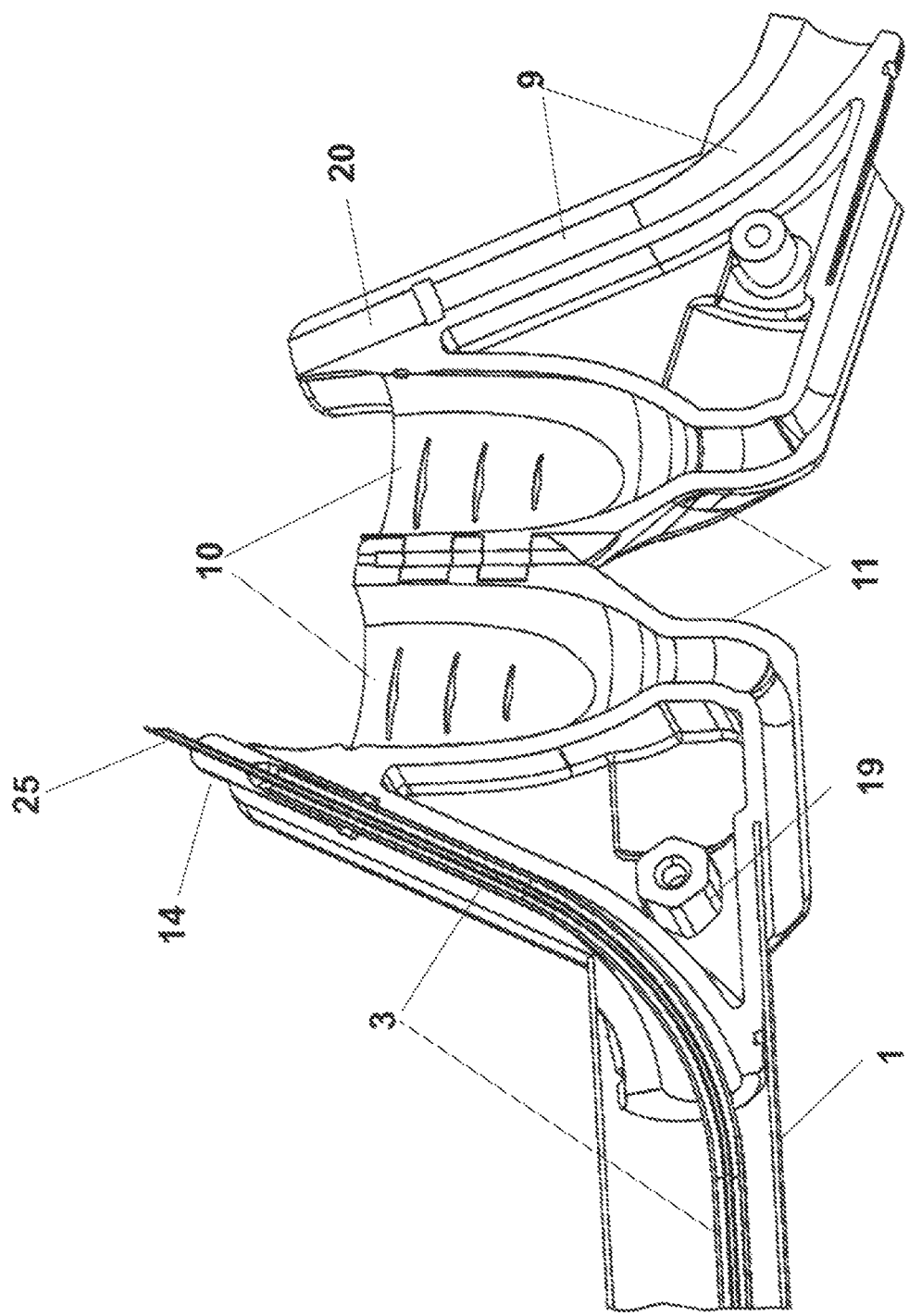
FIG. 6 shows, in perspective view, the segment of a device according to the invention with open ultrasound head support and inserted puncture needle.

FIG. 6 shows, in perspective view, the ultrasound head support 11 in the open state with the twin-lumen puncture needle 25. Clearly depicted are the accommodator 20 for the end cap 14 and the accommodator 9 for the guide pipe 3.

It has been found effective to manufacture this element of the assembly according to the invention from a high-strength sterilizable plastic by means of a 3D printer.

Figure 7:
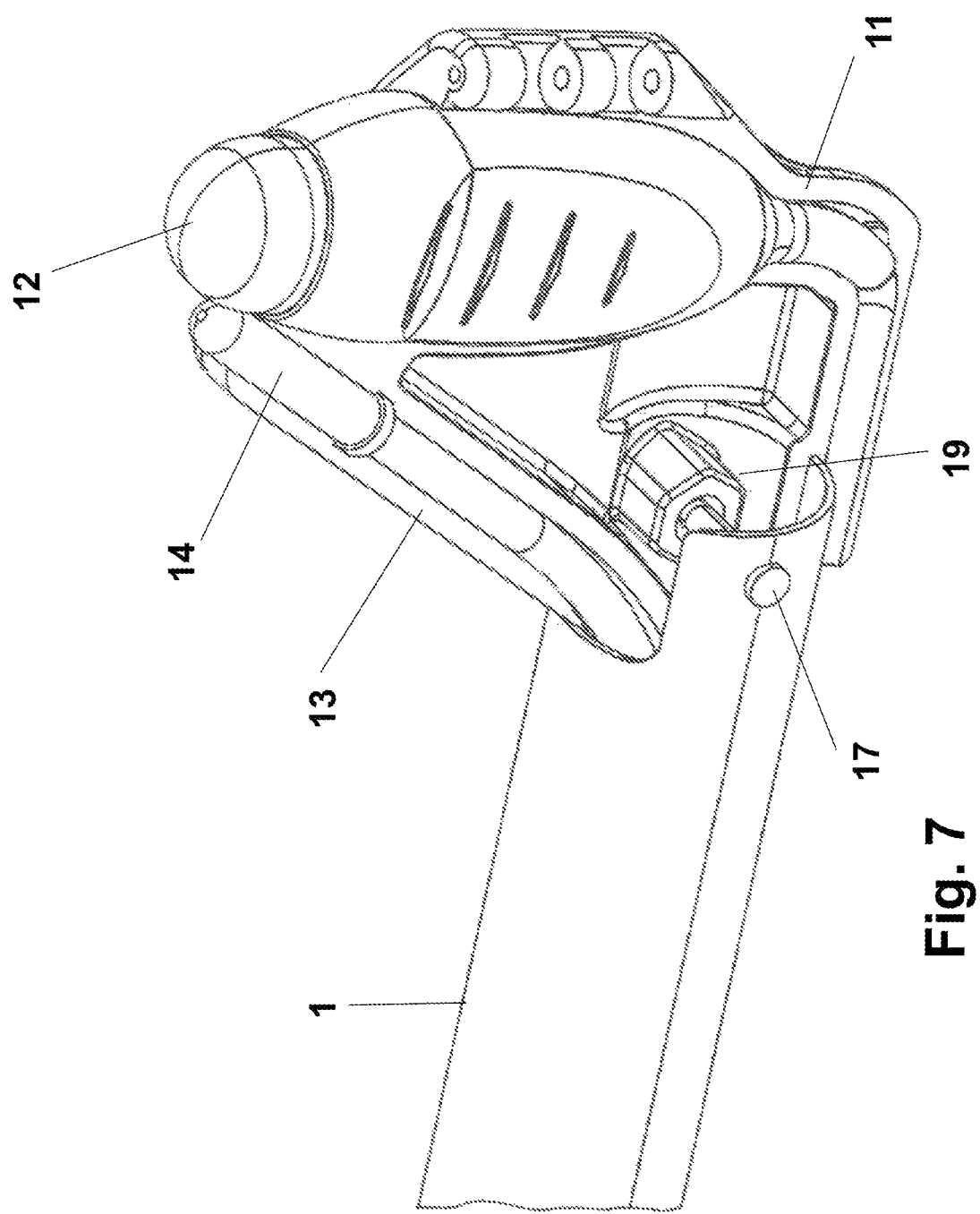
FIG. 7 shows, in perspective view, the segment of a device according to the invention with integrated ultrasound head.

FIG. 7 shows, in perspective view, the end piece of the assembly according to the invention, with the ultrasound head support 11 and the ultrasound head 12 integrated therein as well as the distal end 13 of the guide pipe 3 with the screw-on end cap 14. By means of the screw connection 17, 19, the ultrasound head support 11 is anchored and positioned in the support pipe 1. The ultrasound head 12 is connected to an image reproduction system, which is not depicted here. The connection line is guided along the support pipe 1.

Figure 8:
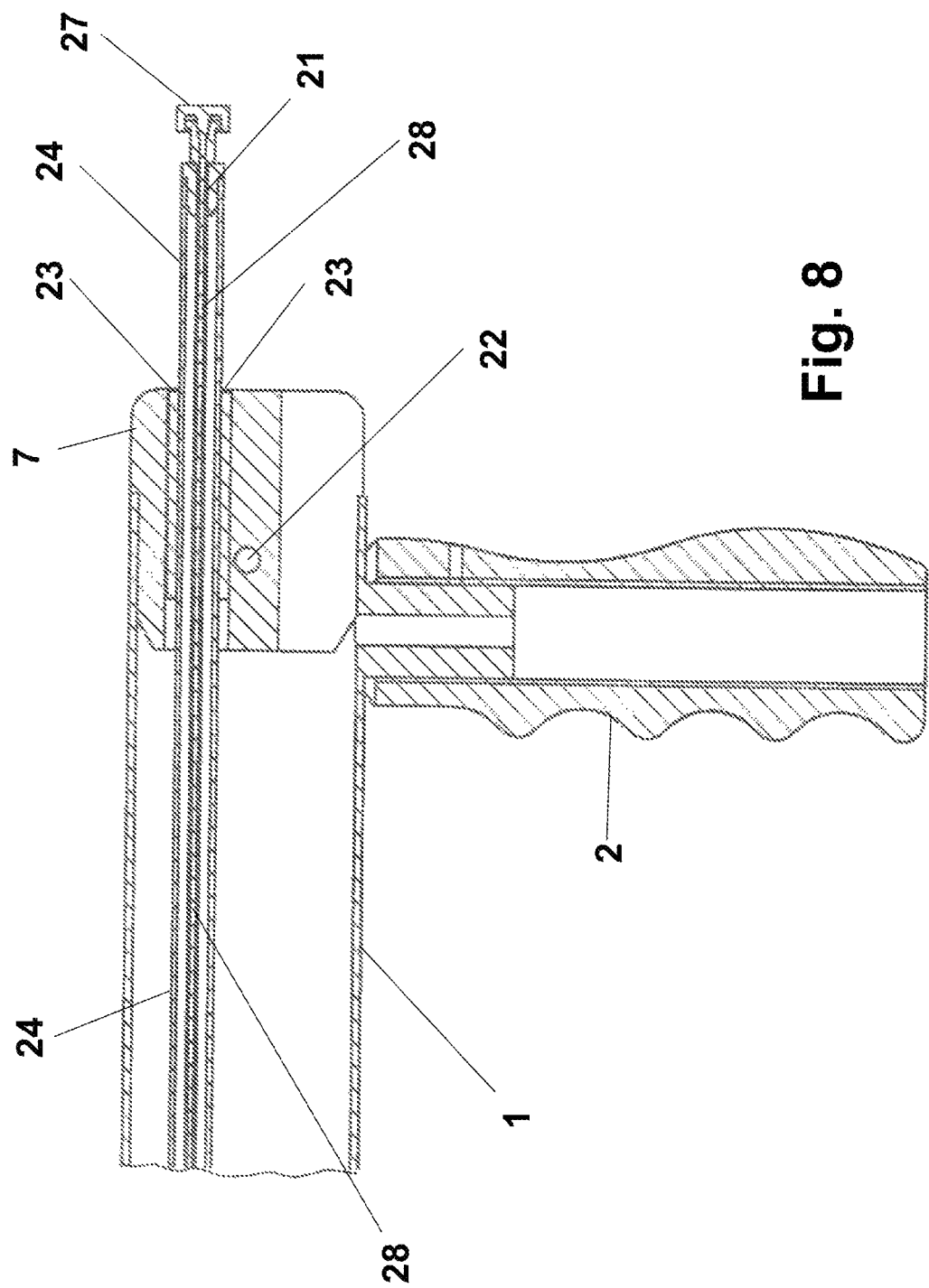
FIG. 8 shows sectionally the proximal segment of the assembly according to the invention for embryo transfer and intrauterine insemination.

FIG. 8 depicts, in section, the proximal end of an assembly according to the invention that is intended for embryo transfer and intrauterine insemination. Such an assembly has the guide pipe 24 and the insertion aid 28 for the single-lumen puncture needle. The guide pipe 24 and the stainless-steel insertion aid 28 reach, from the ultrasound head support 11, up to about 30 mm beyond the end of the end element 7.

In order to ensure that the support pipe 1 and the end element 7 in the assembly can be used both for oocyte recovery and for embryo transfer and intrauterine insemination, the sleeve 23 is provided for the reliable positioning of the guide pipe 24. The fixing element 21 ensures a reliable positioning of the insertion aid 28 which is arranged within the guide pipe 24.

At the end of the insertion aid 28, the screw-on distance element 27 is provided, so that the insertion aid 28 can be manipulated until its distal end protrudes about 2 mm from the end cap 14.

For embryo transfer and intrauterine insemination, the single-lumen puncture needle, not depicted here, having a length of from about 1200 mm to 2000 mm is inserted into the insertion aid 28 and a catheter made of plastic, likewise not depicted here, having a length of from about 1300 mm to 2100 mm is inserted into said puncture needle.

The puncture needle having an outer diameter of about 1.5 mm and an inner diameter of about 1.1 mm and the catheter having an outer diameter of about 1.0 mm and an inner diameter of about 0.5 mm are each manipulatable by hand.

The use of the assembly for oocyte recovery and for embryo transfer and intrauterine insemination at a female rhinoceros shall be described below.

For the intervention in question, the female rhinoceros (there are 6 species and the procedure can be applied to all 6 species) is either hormonally stimulated or the ova are recovered without stimulating the ovaries. Embryo transfer is done on day 2 to 10 after ovulation with the presence of a corpus *luteum* at the ovary. Intrauterine insemination is carried out at the time of the expected ovulation or directly thereafter. The consequence of nonstimulation is that the total yield of ova may be lowered, but the procedure can be repeated at shorter intervals.

General anesthesia is induced in the rhinoceros for the intervention, and said rhinoceros is attended to by a team of anesthetists during the entire procedure.

When the animal comes to rest in the stall on its breastbone or on its side, the feces in the rectum at a length of about 2 m is first manually removed and the intestinal mucosa is then cleaned to remove the fecal particles which are still sticking by means of intensive flushing with tap water via a hose system (supply from water faucet, spontaneous discharge via downward slope). This is followed by the introduction of a commercially available medical mucosa disinfectant in fractions. The disinfection solution (stock solution diluted with tap water as per instructions in order to produce the solution for use) is introduced into the mechanically cleaned intestinal segment in steps of 5 liters and then completely removed again using a discharge hose system. This procedure is repeated 3 times. The rectum is mechanically cleaned and disinfected as a result.

In parallel to these procedures on the rhinoceros, the respective modular assemblies for rhinoceros oocyte recovery, for embryo transfer or for intrauterine insemination are prepared for the intervention—as depicted and described by FIG. 1 to FIG. 8. Part of the oocyte recovery are the additional components of the system, consisting of the medical vacuum pump (from Cook GmbH), the sterile collection container (50 ml tube with screw cap, commercially available from Greiner GmbH) and the 60 ml Luer-Lock syringe filled with commercially available follicle flush liquid (product name: Euroflush). The 60 ml syringe containing the flush liquid is inserted into a mechanical dispensing system (from Steiner, Graz, Austria) with integrated heating function (37° C.) and refilling device and is operated via a foot pedal. The individual components are connected to an integrated vacuum connector (from Gynetics, Belgium) with the aid of a sterile hose system including silicone plug.

For embryo transfer or for intrauterine insemination, use is made of the slightly modified assembly for oocyte recovery. The basic structure of the assembly for embryo transfer differs only marginally from the structure of the assembly for oocyte recovery, with the components such as vacuum pump, sterile collection container or the flush liquid not being required. For transfer or for insemination, the twin-lumen needle is replaced by a longer single-lumen needle.

For the problem-free insertion of the assembly according to the invention into the cleaned and disinfected rectum of the rhinoceros, the front region (sonic head 12, sonic head holder 11 and about 20 cm of the cladding tube 1) is completely coated with a thin layer of sterile medical lubricant (PreSeed, USA). Depending on the size of the animal, the assembly is inserted about 1 m to 1.7 m into the rectum. The ultrasound head 12 arranged at the distal end is, in the present case, connected to the portable ultrasound system (Voluson i, from GE HealthCare GmbH).

For oocyte recovery, both the right and the left ovary are seen. The integrated biopsy function of the ultrasound system (displayed puncture line with length specifications) allows the precise planning of follicle aspiration and flushing.

At each ovary, all follicles of a size of over 5 mm in diameter are then systematically aspirated and, up to 10 times in each case, the aspirated follicle is filled up again to the original size (flushing) and then re-aspirated. This procedure distinctly increases the chances that the ovum is present in the flush liquid. The piercing by the twin-lumen puncture needle 25 into the follicle situated at the ovary is done in each case through the intestinal wall, unless follicles are next to another or among one another. In such a case, they are aspirated using the same access. The twin-lumen needle 25 is, in each case, withdrawn into the support pipe 1 (inner stop) and the position for the next puncture is optimally adjusted by means of the ultrasound image.

The liquid aspirated during a follicle puncture is sterilely recovered in the collection container (volume of 50 ml, placed in a heating system from the Berlin-based company Butter Ingenieurbüro, Germany), wherein switching is, in each case, carried out after attainment of the fill mark of 40 ml in order to avoid suction of the aspiration liquid into the hose system connected to the vacuum pump.

After successful follicle aspiration and flushing, the assembly for oocyte recovery is removed from the rectum.

The procedures in the case of embryo transfer or in the case of intrauterine insemination are identical.

By means of ultrasound monitoring, the distal end of the assembly is positioned above the uterine horn such that the single-lumen needle introduced into the insertion aid 28 can be pierced by hand, with sonographic visual monitoring, through the intestinal wall and the middle of the uterine horn. What is selected is that uterine horn, at the end of which the ovary containing the Graafian follicle or the fresh corpus *luteum* is situated.

The needle tip is positioned exactly inside the uterine cavity in order to then be able to slide a flexible catheter having a length of from about 1300 mm to 2100 mm and an outer diameter of about 1.0 mm by hand through the inner lumen of the positioned single-lumen needle right into the uterine cavity. The catheter composed of a biocompatible material is inserted into the puncture needle with the aid of a funnel-shaped insertion aid attached to the puncture needle without getting stuck. Via this flexible catheter, either the embryo to be transferred or the semen is then transported into the uterine cavity.

The tip of the catheter is rounded and its end is connected to a so-called Luer-Lock connector, which is commercially available. This means that, in the case of insemination, the semen, filled in a 2 ml to 5 ml sterile disposable syringe, can be transported via the catheter into the uterine lumen.

For embryo transfer, the catheter is likewise manually slid several centimeters beyond the needle tip of the single-lumen needle, with sonographic visual monitoring, in the direction of the uterine horn tip.

The tip of the catheter is advanced several centimeters into the uterine lumen in order to achieve some distance from the needle and from possible blood originating from the piercing.

After optimal positioning of the catheter tip, the embryo situated in the catheter is emptied via the connection of a commercial micropipette (20 microliter stroke) with the Luer-Lock connector. Upon pressing of the piston of the micropipette, the embryo situated in a liquid column of about 1 mm in length is gently released into the uterus.

Since semen accounts for a distinctly larger volume (2 ml to 5 ml), a disposable syringe is used instead. The embryo is only sucked into a very small liquid column and is then pressed out from behind by means of the micropipette via an air column.

After embryo transfer or insemination has been carried out, catheter and single-lumen needle are removed in succession from the animal.

Thereafter, it is possible to additionally introduce topically acting antibiotic foam pins (product from cattle production) into the intestine in order to prevent possible local inflammations.

The assembly used in each case is then disassembled, given a rough clean, and disinfected. The individual components are then sterilized.

Following direct ovum recovery at the animal, the ova are searched for in the flush liquid with the aid of a stereomicroscope (from Carl Zeiss Jena GmbH), transferred to a wash solution by means of a micropipette, and then transported to a 2 ml container containing preservation medium for shipment.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims. All methods described herein can be performed in any suitable order unless otherwise indicated herein or otherwise clearly contradicted by context. Various features of the various embodiments disclosed herein can be combined in different combinations to create new embodiments within the scope of the present disclosure. Any ranges given herein include any and all specific values within the range and any and all subranges within the given range.

What is claimed is:

1. An assembly for ultrasound-assisted rectal manipulation at female reproductive organs in large mammals, comprising:
    a support pipe with an end element and a handle piece, the support pipe having a horizontal axis and a distal end,
    a guide pipe provided in the support pipe, the guide pipe having a distal end,
    a puncture needle with a tip, the puncture needle having a twin-lumen construction for a flushing process and an aspiration process, said twin-lumen construction comprising an outer needle and an inner needle,
    a momentum initiator mounted in a movable manner in a horizontal direction in the end element, and
    an ultrasound head support provided at the distal end of the support pipe and having accomodators for an ultrasound head and the distal end of the guide pipe, the ultrasound head having an axis, wherein:
        the axis of the ultrasound head and of the distal end of the guide pipe is in each case angled with respect to the horizontal axis of the support pipe such that the tip of the puncture needle is in an ultrasound scan range of the ultrasound head,
        the guide pipe is positioned in the support pipe by means of a fitted positioning element,
        the puncture needle is arranged in the guide pipe in a movable manner, is connected via its proximal end to the momentum initiator in a detachable manner and is fixed in said momentum initiator,
        and
        connecting pieces are provided at the proximal end of the twin-lumen puncture needle for the outer and inner needles, said connecting pieces being connectable to a medical flushing device and to a vacuum pump and a receptacle by means of pieces of tubing,
        wherein the assembly is configured for rectal manipulation of female reproductive organs of large mammals.

2. The assembly as claimed in claim 1, wherein the axis of the ultrasound head is arranged at an angle of from 30° to 90° in relation to the horizontal axis of the support pipe.

3. The assembly as claimed in claim 1, wherein a positioning element for the guide pipe has a funnel-shaped receiver for assisting the insertion of the twin-lumen puncture needle into the guide pipe.

4. The assembly as claimed in claim 1, wherein the ultrasound head support is connected to the support pipe in a detachable manner.

5. The assembly as claimed in claim 1, wherein the twin-lumen puncture needle is surrounded by a piece of plastic tubing in order to increase slidability in the guide pipe and/or the guide pipe has at its distal end a screw-on end cap.

6. The assembly as claimed in claim 1, wherein the momentum initiator is slit at a distal end.

7. The assembly as claimed in claim 1, wherein the connection between the proximal end of the twin-lumen puncture needle and the momentum initiator is established by means of a sleeve retainer which can be screwed onto the momentum initiator.

8. The assembly as claimed in claim 1, wherein a route of the puncture needle is limited by providing on the momentum initiator two stop elements, with one stop element within the support pipe and one stop element outside the support pipe.

9. The assembly as claimed in claim 1, wherein there is provided on the momentum initiator a locking element with bayonet lock or locking screw.

10. The assembly as claimed in claim 1, wherein the guide pipe is coated with a plastic suitable therefore in order to increase slidability.

11. The assembly as claimed in claim 1, wherein a guidable route of the momentum initiator is between 60 mm and 120 mm.

12. An assembly for rectal oocyte recovery in large mammals, the assembly comprising:
    a support pipe with an end element and a handle piece, the support pipe having a horizontal axis and a distal end,
    a guide pipe provided in the support pipe, the guide pipe having a distal end,
    a puncture needle with a tip, the puncture needle having a twin-lumen construction for a flushing process and an aspiration process, said twin-lumen construction comprising an outer needle and an inner needle,
    a momentum initiator mounted in a movable manner in a horizontal direction in the end element, and
    an ultrasound head support provided at the distal end of the support pipe and having accommodators for an ultrasound head and the distal end of the guide pipe, the ultrasound head having an axis, wherein:

the axis of the ultrasound head and of the distal end of the guide pipe is in each case angled with respect to the horizontal axis of the support pipe such that the tip of the puncture needle is in an ultrasound scan range of the ultrasound head, which is connected to an image reproduction device, and the guide pipe is positioned in the support pipe by means of a fitted positioning element, the puncture needle is arranged in the guide pipe in a movable manner, is connected via its proximal end to a momentum initiator in a detachable manner and is fixed in said momentum initiator, and there are connecting pieces at the proximal end of the twin-lumen puncture needle for the outer and inner needles, said connecting pieces being connectable to a medical flushing device and to a vacuum pump and a receptacle by means of pieces of tubing, wherein the assembly is configured for rectal manipulation of female reproductive organs of large mammals.

13. An assembly for embryo transfer and intrauterine insemination of mammals, the assembly comprising:

a support pipe with an end element and a handle piece, the support pipe having a horizontal axis, a length, and a distal end, a guide pipe provided in the support pipe, the guide pipe having a proximal end, a single-lumen puncture needle with a tip, and an ultrasound head support provided at the distal end of the support pipe and having accomodators for an ultrasound head and a distal end of the guide pipe, the ultrasound head having an axis, wherein:

the axis of the ultrasound head and of the distal end of the guide pipe is in each case angled with respect to the horizontal axis of the support pipe such that the tip of the single-lumen puncture needle is in an ultrasound scan range of the ultrasound head, which is connected to an image reproduction device, and the guide pipe is approximately the length of the support pipe and is mounted at a proximal end of the support pipe in the end element, there is provided within the guide pipe an insertion aid, in which the single-lumen puncture needle is arranged in a horizontally movable manner, and there is provided in said puncture needle a movable catheter, which is provided at a proximal end of the catheter with a Luer-Lock connector.

14. A device for rectally collecting oocytes in large mammals comprising:

a support pipe with an end element and a handle piece, the support pipe having a horizontal axis and a distal end, a momentum initiator mounted in a movable manner in a horizontal direction in the end element, and a guide pipe mounted in the support pipe by means of a fitted positioning element, wherein:

a twin-lumen puncture needle for a flushing process and aspiration process is arranged in the guide pipe in a movable manner, said twin-lumen puncture needle having a tip and comprising an outer needle and an inner needle, wherein the puncture needle is connected via its proximal end to the momentum initiator in a detachable manner, the momentum initiator having at another end a grip element, connecting pieces present at the proximal end of the twin-lumen puncture needle for the outer and inner needles are connectable to a medical flushing device and to a vacuum pump and a container for accommodation of aspirated oocytes by means of pieces of tubing, an ultrasound head support is provided at the distal end of the support pipe for accommodation of an ultrasound head and a distal end of the twin-lumen puncture needle, and an axis of the ultrasound head and a distal end of the guide pipe are each angled with respect to the horizontal axis of the support pipe, wherein the guide pipe is angled depending on the axis of the ultrasound head such that the tip of the twin-lumen puncture needle is in an ultrasound scan range during collection of the oocytes, wherein the device is configured for rectal manipulation of female reproductive organs of large mammals.

15. An assembly for ultrasound-assisted manipulation at female reproductive organs of large mammals comprising:

a support pipe with an end element and a handle piece, the support pipe having a horizontal axis, a length, and a distal end, a guide pipe provided in the support pipe, the guide pipe having a distal end and a proximal end, a single-lumen puncture needle with a tip, and an ultrasound head support provided at the distal end of the support pipe and having accomodators for an ultrasound head and the distal end of the guide pipe, the ultrasound head having an axis, wherein:

the axis of the ultrasound head and of the distal end of the guide pipe is in each case angled with respect to the horizontal axis of the support pipe such that the tip of the single-lumen puncture needle is in an ultrasound scan range of the ultrasound head, the guide pipe is approximately the length of the support pipe and is mounted at a proximal end of the support pipe in the end element, there is provided within the guide pipe an insertion aid, in which the single-lumen puncture needle is arranged in a horizontally movable manner, and there is provided in the single-lumen puncture needle a movable catheter, which is provided at a proximal end of the catheter with a Luer-Lock connector.

16. The assembly as claimed in claim 15, wherein the axis of the ultrasound head is arranged at an angle of from 30° to 90° in relation to the horizontal axis of the support pipe.

17. The assembly as claimed in claim 15, wherein the ultrasound head support is connected to the support pipe in a detachable manner.

18. The assembly as claimed in claim 15, wherein the guide pipe and the insertion aid have a two-part construction and can be connected to one another in a detachable manner.

19. The assembly as claimed in claim 15, wherein the guide pipe is coated with a plastic suitable therefore in order to increase slidability.

20. The assembly as claimed in claim 15, wherein the single-lumen puncture needle and the catheter are mounted such that they are guidable by hand and/or a disposable syringe or a micropipette is provided within the catheter.

* * * * *